US012599646B2

(12) United States Patent
Evans et al.

(10) Patent No.: US 12,599,646 B2
(45) Date of Patent: Apr. 14, 2026

(54) PEPTIDE-CONTAINING COMPOSITION FOR USE FOR TREATING NEOPLASTIC LESIONS

(71) Applicant: CYTOVATION ASA, Bergen (NO)

(72) Inventors: Charles Evans, Godalming (GB); Cameron Stevenson, Guildford (GB); Suzanne Edmunds, Guildford (GB)

(73) Assignee: CYTOVATION ASA, Bergen (NO)

( * ) Notice: Subject to any disclaimer, the term of this patent is extended or adjusted under 35 U.S.C. 154(b) by 111 days.

(21) Appl. No.: 17/791,270

(22) PCT Filed: Mar. 10, 2020

(86) PCT No.: PCT/EP2020/056324
§ 371 (c)(1),
(2) Date: Jul. 7, 2022

(87) PCT Pub. No.: WO2021/139901
PCT Pub. Date: Jul. 15, 2021

(65) Prior Publication Data

US 2023/0052378 A1 Feb. 16, 2023

(30) Foreign Application Priority Data

Jan. 7, 2020 (GB) ...................................... 2000167

(51) Int. Cl.

| | |
|---|---|
| ***A61K 38/03*** | (2006.01) |
| ***A61K 9/00*** | (2006.01) |
| ***A61K 9/06*** | (2006.01) |
| ***A61K 9/08*** | (2006.01) |
| ***A61K 9/10*** | (2006.01) |
| ***A61K 47/10*** | (2017.01) |
| ***A61K 47/14*** | (2017.01) |
| ***A61K 47/24*** | (2006.01) |
| ***A61K 47/44*** | (2017.01) |
| ***A61P 17/12*** | (2006.01) |

(52) U.S. Cl.
CPC ............ *A61K 38/03* (2013.01); *A61K 9/0014* (2013.01); *A61K 9/10* (2013.01); *A61K 47/10* (2013.01); *A61K 47/44* (2013.01); *A61P 17/12* (2018.01)

(58) Field of Classification Search
CPC ........ A61K 38/03; A61K 47/10; A61K 47/14; A61K 47/24; A61K 47/44; A61K 9/0014; A61K 9/06; A61K 9/08; A61K 9/10; A61P 17/12
See application file for complete search history.

(56) References Cited

U.S. PATENT DOCUMENTS 11,622,945 B2 4/2023 Sonti et al.

FOREIGN PATENT DOCUMENTS

| | | |
|---|---|---|
| WO | 2011/040894 A1 | 4/2011 |
| WO | 2011/092347 A1 | 8/2011 |
| WO | 2019/243471 A1 | 12/2019 |

OTHER PUBLICATIONS

HPV Infection from Mayo Clinic, https://www.mayoclinic.org/diseases-conditions/hpv-infection/symptoms-causes/syc-20351596, pp. 1-24, accessed Jul. 17, 2025. (Year: 2025).*

Polyoxyl20cetostearylether from FDA.gov, https://precision.fda.gov/ginas/app/ui/substances/b9b1dff8-554f-4d59-8d3c-2129f7c4fcc2, pp. 1-3, enclosed, accessed Jul. 16, 2025. (Year: 2025).*

Office Action issued on Nov. 9, 2024, in Chinese Patent Application No. 202080092074.6.

Lin et al., "Research progress on the treatment of skin warts", Clinical Misdiagnosis & Mistherapy, vol. 29, No. 5 (2016).

Office Action issued in corresponding Canadian application No. 3,163,417, Oct. 25, 2023, 3 pages.

International Search Report and Written Opinion issued for Application No. PCT/EP2020/056324, dated Nov. 11, 2020, 16 pages.

Bruggink, Sjoerd C., et al. "Cutaneous wart-associated HPV types: prevalence and relation with patient characteristics." Journal of Clinical Virology 55.3 (2012): 250-255.

Edgar, Robert C. "MUSCLE: multiple sequence alignment with high accuracy and high throughput." Nucleic acids research 32.5 (2004): 1792-1797.

Lipke, Michelle M. "An armamentarium of wart treatments." Clinical medicine & research 4.4 (2006): 273-293.

Lowy, Douglas R., and John T. Schiller. "Prophylactic human papillomavirus vaccines." The Journal of clinical Investigation 116.5 (2006): 1167-1173.

Rice, Peter, Ian Longden, and Alan Bleasby. "EMBOSS: the European molecular biology open software suite." Trends in genetics 16.6 (2000): 276-277.

Rowe, Raymond C., Paul Sheskey, and Marian Quinn. Handbook of pharmaceutical excipients. Libros Digitales-Pharmaceutical Press, 2009. 917 pages.

Sievers, Fabian, et al. "Fast, scalable generation of high-quality protein multiple sequence alignments using Clustal Omega." Molecular systems biology 7.1 (2011): 539.

Sterling, Jane C., et al. "British Association of Dermatologists' guidelines for the management of cutaneous warts 2014." British Journal of Dermatology 171.4 (2014): 696-712.

* cited by examiner

*Primary Examiner* — Julie Ha
(74) *Attorney, Agent, or Firm* — Meunier Carlin & Curfman LLC

(57) ABSTRACT

The present invention provides a pharmaceutical composition comprising the therapeutic peptide CyPep-1, for use in treating neoplastic lesions, in particular warts.

16 Claims, 2 Drawing Sheets

Figure 1:
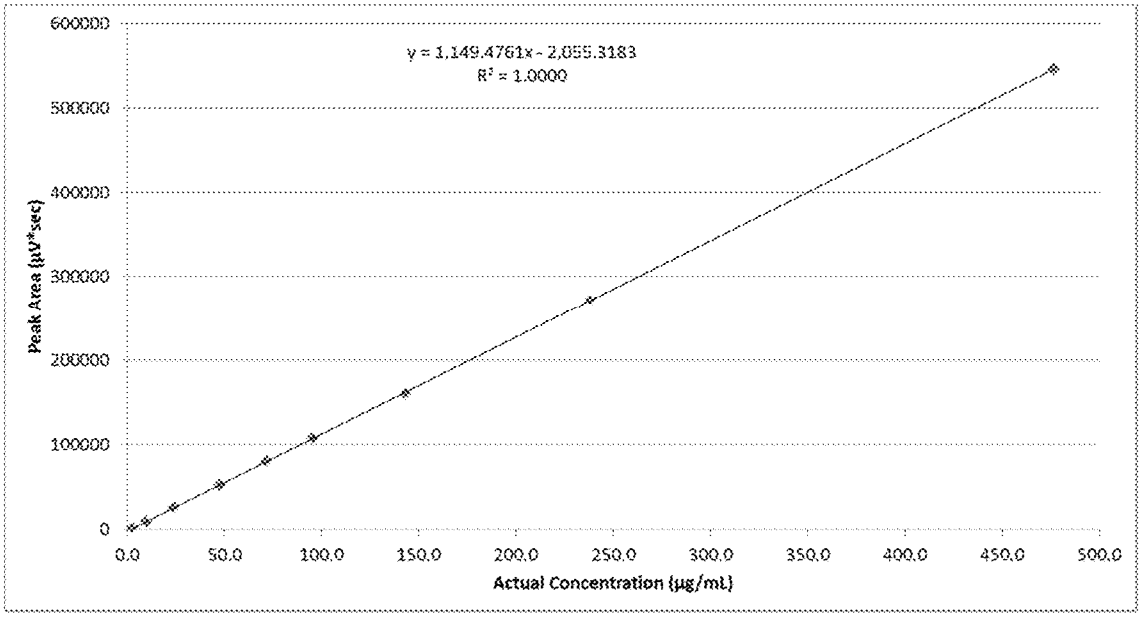
Figure 1:
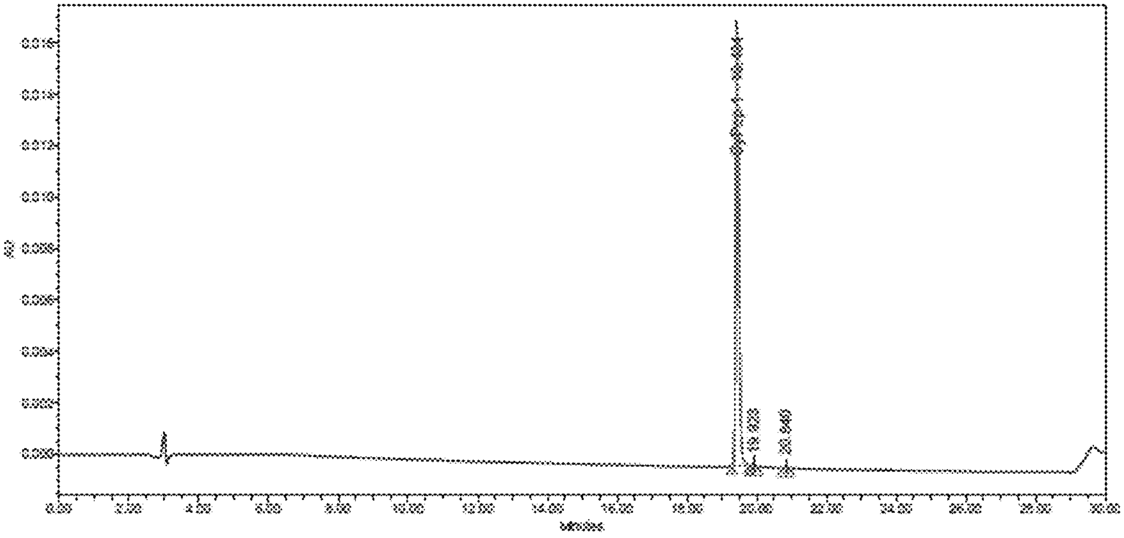

Specification includes a Sequence Listing.

A

B

SEQUENCE LISTING

```
<160> NUMBER OF SEQ ID NOS: 3

<210> SEQ ID NO 1
<211> LENGTH: 27
<212> TYPE: PRT
<213> ORGANISM: Artificial Sequence
<220> FEATURE:
<223> OTHER INFORMATION: CyPep-1

<400> SEQUENCE: 1

Tyr Gly Arg Lys Lys Arg Arg Gln Arg Arg Arg Gly Lys Thr Leu Arg
1               5                   10                  15

Val Ala Lys Ala Ile Tyr Lys Arg Tyr Ile Glu
            20                  25
```

-continued

```
<210> SEQ ID NO 2
<211> LENGTH: 15
<212> TYPE: PRT
<213> ORGANISM: Homo sapiens

<400> SEQUENCE: 2

Lys Thr Leu Arg Val Ala Lys Ala Ile Tyr Lys Arg Tyr Ile Glu
1               5                   10                  15


<210> SEQ ID NO 3
<211> LENGTH: 12
<212> TYPE: PRT
<213> ORGANISM: Human immunodeficiency virus type 1

<400> SEQUENCE: 3

Tyr Gly Arg Lys Lys Arg Arg Gln Arg Arg Arg Gly
1               5                   10
```

PEPTIDE-CONTAINING COMPOSITION FOR USE FOR TREATING NEOPLASTIC LESIONS

The present invention provides a pharmaceutical composition for the treatment of warts or other neoplastic lesions, comprising as active ingredient a therapeutic peptide based on the sequence of the peptide CyPep-1, which has the amino acid sequence of SEQ ID NO:1. Also provided by the present invention are methods of treating warts or other neoplastic lesions using the composition of the invention.

Warts are benign skin tumours (lesions) caused by infection with human papillomavirus (HPV). The common wart (verruca vulgaris) tends to present as a small, hard, rough growth on the skin, most commonly on the hands. If present on the sole of the foot, a wart is generally referred to as a verruca (verruca plantaris). Warts commonly develop on the genitalia or anus, in which case they are known as anogenital warts (*Condylomata acuminata*). Other, less common types of wart include flat warts (verruca plana), which most commonly occur on the face or neck, hands, wrists and knees; filiform warts, which commonly form on the face; and periungual warts, which present in clusters around the fingernail or toenail.

Warts are generally believed to arise when damaged skin is exposed to HPV, allowing the virus to access basal keratinocytes, which are the primary target for HPV infection of the skin. Both direct and indirect person-to-person transmission of warts occurs by shedding of HPV from a wart (Lipke, Clinical Medicine and Research 4(4): 273-293, 2006). Different HPV serotypes are associated with different types of warts: for instance, cutaneous common warts and verrucas are most frequently caused by HPV types 27, 57, 2 and 1 (Bruggink et al., Journal of Clinical Virology 55(3): 250-255, 2012), while genital warts are most commonly caused by HPV types 6 and 11 (Lowy & Schiller, Journal of Clinical Investigation 116(5): 1167-1173, 2006).

Warts are very common, and it is believed that they majority of individuals will suffer from warts at some point during their lives. While in some cases warts may be considered harmless, the majority of sufferers find them uncomfortable, while many wart sufferers also find their warts embarrassing, such that their quality of life is damaged (Lipke, supra). However, there is a shortage of effective treatments for warts—while several wart treatments exist (e.g. salicylic acid, cryotherapy, laser treatment, 5-fluorouracil, etc.), the majority of treatments lack evidence of their efficacy (Sterling et al., British Journal of Dermatology 171: 696-712, 2014). In the absence of successful treatment, warts are generally self-limiting, but can take up to two years to heal. Even with apparently successful treatment, recurrence of warts is common. Thus new treatments for warts are needed. New treatments for other neoplastic lesions would also be beneficial.

WO 2011/092347 discloses anti-neoplastic peptides, including CyPep-1, which consists of the amino acid sequence set forth in SEQ ID NO: 1. As shown in WO 2011/092347, CyPep-1 is selectively cytotoxic to neoplastic cells, and co-pending application PCT/EP2019/066295 demonstrates that CyPep-1 is highly effective in treating cancer when used in combination with a checkpoint inhibitor. It has been found that CyPep-1 is particularly effective for treatment of warts.

CyPep-1 is a fusion peptide based on a fragment of the tumour suppressor protein Conductin/Axin2 coupled to the C-terminus of the HIV-TAT cell-penetrating peptide. The HIV-TAT cell-penetrating peptide is a cationic peptide, and without being bound by theory, it is believed that the selective cytotoxicity of CyPep-1 for neoplastic cells is due to the negative charge held by neoplastic cell membranes (in contrast, healthy mammalian cells tend to have membranes with a more neutral charge). Beneficially, CyPep-1 drives lysis of target cells, resulting in release of cellular contents upon cell death. In the context of an HPV-infected wart cell, this includes the release of HPV antigens. The immune system is exposed to released HPV antigens, driving a T-cell response which results not only in destruction of the wart, but also leads to long-lasting immunity to HPV (or at least the infecting HPV strain). Treatment of warts with CyPep-1 therefore not only destroys existing warts, but also prevents or reduces the probability of their recurrence.

CyPep-1 also has antibacterial properties (possibly also due to the negative charge held by many bacterial cell membranes), and has been shown to have a potent bacteriocidal effect against medically-relevant species of Gram-positive and Gram-negative bacteria (see WO 2011/092347).

The present invention provides a CyPep-1 composition which is suitable for treating warts, or indeed other neoplasms. The composition has been shown to have particularly advantageous properties in terms of the solubility and stability of CyPep-1 therein, and slow release of CyPep-1 which limits the frequency of application of CyPep-1 required for successful wart treatment. Use of this CyPep-1 formulation in wart treatment has been found to be effective.

Accordingly, in a first aspect, the invention provides a pharmaceutical aqueous composition comprising:

(i) 0.1-5% therapeutic oligopeptide, wherein the therapeutic oligopeptide comprises the amino acid sequence set forth in SEQ ID NO: 1, or an amino acid sequence having at least 85% sequence identity thereto;
(ii) 0.1-5% preservative;
(iii) 0.1-5% silicone;
(iv) 10-20% di(ethylene glycol) ethyl ether;
(v) 0.005-0.1% butylated hydroxyanisole;
(vi) 1-10% liquid paraffin;
(vii) 1-10% soft paraffin;
(viii) 1-10% cetostearyl alcohol; and
(ix) 0.1-5% polyoxyl 20 cetostearyl ether.

The composition of the invention is suitable for wart treatment, though may also be used for other purposes, as described below.

In another aspect, the invention provides a composition as described above for use in therapy.

In another aspect, the invention provides a composition as described above for use in the treatment of a neoplasm on a surface of the body, e.g. a neoplasm of the skin.

Particularly, the composition may be for the treatment of warts. In another embodiment it may for the treatment of a skin cancer.

In a related aspect, the invention provides a method of treating a neoplasm, e.g. a wart, in a subject, comprising administering a composition as described above.

In another related aspect, the invention provides the use of a composition as described above in the manufacture of a medicament for treating a neoplasm, e.g. a wart.

In the composition set out above, the amount of each ingredient is set out as the percentage content of the ingredient within the composition of the invention. In the composition set out above, and throughout this specification, all percentage content values denote the percentage weight by weight (% w/w).

Thus the present invention provides a pharmaceutically-acceptable composition for delivery of the therapeutic peptide. This may have particular utility in the context of wart treatment. That is to say, the composition provided herein is suitable for treating warts. "Pharmaceutical" or "pharmaceutically-acceptable" as used herein indicates that the composition is physiologically acceptable to a recipient to whom the composition is administered. The composition of the present invention is a cream suitable for topical administration (i.e. administration to the skin). Thus the composition of the invention is a pharmaceutically-acceptable cream. As a cream, the composition of the invention is semi-solid. A pharmaceutically-acceptable cream is non-toxic, and preferably non-irritant, as well as providing a suitable vehicle for delivery of the active ingredient (discussed below), particularly to a target wart. As a pharmaceutical cream, the composition of the invention is an emulsion comprising an aqueous phase and an oil phase. The composition of the invention may in particular be an oil-in-water emulsion. The composition of the invention is preferably sterile.

The composition of the invention is an aqueous composition. An aqueous composition, as referred to herein, is a composition containing water, or made up with water. In other words, the composition of the invention comprises an active agent and various excipients as described below, plus water. Although the composition is aqueous, this does not mean that all components of the composition are dissolved in water—rather, the composition is an emulsion containing both an aqueous phase and an oil phase, as detailed above. However, as an aqueous composition, the water generally forms the continuous phase of the emulsion, meaning that the emulsion is an oil-in-water emulsion, as specified above. Where the composition of the invention is described herein, and the percentage content of each excipient does not (or may not) add up to 100%, the balance (i.e. the remainder) of the composition is water.

As mentioned above, the composition of the invention is suitable for treating neoplasms. A "neoplasm" is broadly defined to include any malignant, pre-malignant or non-malignant neoplastic condition. A neoplasm may be characterised by uncontrolled or unwanted cellular proliferation. The neoplasm may particularly be a neoplasm of the skin, including skin cancer or a non-malignant skin neoplasm, or a neoplasm occurring on a surface or area of the body to which a cream may be applied. More particularly the composition is suitable for treating warts. The term "wart" as defined herein encompasses all kinds of wart, as discussed further below. Treatment of warts, or other neoplasms, using the composition of the invention is achieved by means of its active ingredient. The term "active ingredient" is used to refer to the component of the composition which has the therapeutic effect, i.e. the anti-neoplastic or anti-wart effect. The active ingredient in the composition of the invention is a therapeutic oligopeptide. Upon administration of the composition of the invention to a wart or other neoplasm on a subject, the therapeutic oligopeptide comes into contact with the wart or other neoplasm, and destroys the wart or other neoplasm. Thus the therapeutic oligopeptide used in the present invention has anti-wart activity, or more generally, activity against neoplastic cells.

The therapeutic oligopeptide used in the composition of the invention comprises the amino acid sequence set forth in SEQ ID NO: 1, or an amino acid sequence having at least 85% sequence identity to SEQ ID NO: 1. As detailed above, the therapeutic oligopeptide of SEQ ID NO: 1 (CyPep-1) is disclosed in WO 2011/092347. SEQ ID NO: 1 consists of a fragment of the tumour suppressor protein Conductin/Axin2 coupled to the C-terminus of the HIV-TAT cell-penetrating peptide. The aforementioned fragment of Conductin/Axin2 has the amino acid sequence set forth in SEQ ID NO: 2 (corresponding to amino acid numbers 13-27 of SEQ ID NO: 1) and the HIV-TAT cell-penetrating peptide has the amino acid sequence set forth in SEQ ID NO: 3 (corresponding to amino acid numbers 1-12 of SEQ ID NO: 1).

An oligopeptide is a polymer formed from amino acids joined to one another by peptide bonds. As defined herein, an oligopeptide comprises at least three amino acids, though clearly a therapeutic oligopeptide as used herein comprises more than three amino acids. An oligopeptide as defined herein has no particular maximum length, e.g. it may comprise up to 30, 40, 50 or 100 amino acids or more, but typically the prefix "oligo" is used to designate a relatively small number of amino acid subunits, i.e. less than 200, preferably less than 100, 90, 80, 70, 60 or 50 amino acids. The therapeutic oligopeptide used in the composition of the invention may thus comprise at least 23 and no more than 200 amino acids. In embodiments it comprises at least 24, 25, 26 or 27 amino acids. Alternatively defined it comprises no more than 50, 45, 40, 35, 30, 29, 28 or 27 amino acids. The therapeutic oligopeptide may thus comprise a number of amino acids in a range composed of any of the integers set out above for a minimum or maximum number of sub-units. Representative subunit ranges thus include 23-150, 23-100, 23-80, 23-50, 23-40, 23-30, 25-150, 25-100, 25-80, 25-50, 25-40, 25-30, 26-150, 26-100, 26-80, 26-50, 26-40, 26-30, 27-150, 27-100, 27-80, 27-50, 27-40, 27-30, 27-29 and 27-28.

The therapeutic oligopeptide used in the composition of the present invention comprises the amino acid sequence set forth in SEQ ID NO: 1, or an amino acid sequence having at least 85%, 90% or 95% sequence identity thereto. In a particular embodiment, the therapeutic oligopeptide comprises the amino acid sequence set forth in SEQ ID NO: 1. In another embodiment, the therapeutic oligopeptide consists of the amino acid sequence set forth in SEQ ID NO: 1, or an amino acid sequence having at least 85%, 90% or 95% sequence identity thereto. In another embodiment, the therapeutic oligopeptide consists of the amino acid sequence set forth in SEQ ID NO: 1.

The level of sequence identity between two sequences (e.g. an oligopeptide sequence of interest and the sequence set forth in SEQ ID NO: 1) may be determined by performing a sequence alignment. A sequence alignment may be performed using any suitable method, for instance a computer programme such as EMBOSS Needle or EMBOSS stretcher (both Rice, P. et al., Trends Genet. 16(6): 276-277, 2000) may be used for pairwise sequence alignments while Clustal Omega (Sievers, F. et al., Mol. Syst. Biol. 7:539, 2011) or MUSCLE (Edgar, R. C., Nucleic Acids Res. 32(5):1792-1797, 2004) may be used for multiple sequence alignments. Such computer programmes may be used with the standard input parameters, e.g. the standard Clustal Omega parameters: matrix Gonnet, gap opening penalty 6, gap extension penalty 1; or the standard EMBOSS Needle parameters: matrix BLOSUM62, gap opening penalty 10, gap extension penalty 0.5. Any other suitable parameters may alternatively be used. A sequence alignment must be performed globally, i.e. across the entire length of the sequences compared.

The therapeutic oligopeptide used in the present invention may comprise only proteinogenic amino acids (i.e. the L-amino acids encoded by the standard genetic code). Alternatively the therapeutic oligopeptide used according to the present invention may comprise one or more non-proteinogenic amino acids. For instance, the therapeutic oligopeptide used according to the invention may comprise one or more D-amino acids (e.g. at least 1, 2, 3, 4, 5, 6, 7, or 8 or more D-amino acids), human-engineered amino acids or natural non-proteinogenic amino acids, e.g. amino acids formed through metabolic processes. Examples of non-proteinogenic amino acids which may be used include ornithine (a product of the urea cycle) and artificially-modified amino acids such as 9H-fluoren-9-ylmethoxycarbonyl (Fmoc)-, tert-Butyloxycarbonyl (Boc)-, and 2,2,5,7,8-pentamethyl-chromane-6-sulphonyl (Pmc)-protected amino acids, and amino acids having the carboxybenzyl (Z) group.

In vitro and/or in vivo stability of the therapeutic oligopeptide may be improved or enhanced through the use of stabilising or protecting means known in the art, for example the addition of protecting or stabilising groups, incorporation of amino acid derivatives or analogues or chemical modification of amino acids. Such protecting or stabilising groups may for example be added at the N- and/or C-terminus. An example of such a group is an acetyl group and other protecting groups or groups which might stabilise a peptide are known in the art.

A peptide consisting wholly of L-amino acids is known in the art as an L-peptide, while a peptide consisting wholly of D-amino acids is known in the art as a D-peptide. The term "inverso-peptide" is used to refer to a peptide with the same amino acid sequence as an L-peptide, but consisting wholly of D-amino acids (i.e. a D-peptide with the same sequence as a corresponding L-peptide). An inverso-peptide has a mirrored structure to its corresponding L-peptide (i.e. an L-peptide of the same amino acid sequence). Inverso-peptides can be advantageous for use in a clinical setting (relative to L-peptides) because they are not generally susceptible to degradation by serum proteases (due to their unnatural conformation inverso-peptides may not be recognised by protease enzymes). In a particular embodiment, the therapeutic oligopeptide used according to the invention is an inverso compound, every amino acid of which is a D-amino acid. That is to say the therapeutic oligopeptide may be a D-peptide. The oligopeptidic compound may in particular comprise or consist of a D-peptide consisting of the amino acid sequence set forth in SEQ ID NO: 1.

A therapeutic oligopeptide as used herein may be synthesised by the skilled person using standard biochemical techniques. If the oligopeptide is an L-peptide comprising only proteinogenic amino acids, it may be synthesised by recombinant DNA technology. That is to say, a DNA sequence encoding the oligopeptide may be cloned and introduced into an expression vector. A DNA sequence encoding a therapeutic oligopeptide as used herein comprises or consists of a nucleotide sequence which encodes the amino acid sequence set forth in SEQ ID NO: 1, or an amino acid sequence having at least 85%, 90% or 95% sequence identity thereto. Such a nucleotide sequence may be generated and synthesised by the skilled person without difficulty.

A DNA sequence encoding the therapeutic oligopeptide used herein may be generated by amplification from a template, e.g. by PCR, or by artificial gene synthesis, using standard methods known in the art. The DNA sequence encoding the oligopeptide may then be introduced into an expression vector, using standard molecular cloning techniques such as restriction enzymes or Gibson assembly. Suitable expression vectors are known in the art. The expression vector may then be introduced into a cellular expression system using standard techniques. Suitable expression systems may include bacterial cells and/or eukaryotic cells such as yeast cells, insect cells or mammalian cells. Given that the therapeutic oligopeptide used herein may be toxic to bacterial cells (as discussed above), a eukaryotic cell may be a more appropriate cellular expression system for production of the oligopeptidic compound.

Instead of a cellular expression system, a cell-free, in vitro protein expression system may be used to synthesise an L-peptide compound as used herein. In such a system a nucleotide sequence encoding the oligopeptide is transcribed into mRNA, and the mRNA translated into a protein, in vitro. Cell-free expression system kits are widely commercially available, and can be purchased from e.g. THERMO FISHER SCIENTIFIC® (USA).

Oligopeptides to be used in the invention may alternatively be chemically synthesised in a non-biological system. Oligopeptides which comprise D-amino acids or other non-proteinogenic amino acids may in particular be chemically synthesised, since biological synthesis is generally not possible in this case. Liquid-phase protein synthesis or solid-phase protein synthesis may be used to generate polypeptides which may form or be comprised within the oligopeptidic compounds for use in the invention. Such methods are well-known to the skilled person, who can readily produce oligopeptides using appropriate methodology common in the art.

As noted above, the therapeutic oligopeptide used in the composition of the invention has anti-wart activity. This means that when the therapeutic oligopeptide is applied to a wart on a subject, over a period of time (e.g. at least 4 weeks), healing of the wart results. For instance the wart may shrink or fall off, and/or the skin forming the wart may return to normal. To determine whether an oligopeptide has anti-wart activity, a composition comprising an oligopeptide of interest may be applied to warts on several subjects, and the results compared to results obtained with subjects treated with a placebo (i.e. an otherwise identical composition or cream lacking the oligopeptide of interest). If superior results are obtained with the composition containing the oligopeptide of interest than with the placebo, the oligopeptide of interest can be considered to have anti-wart activity, and thus to constitute a therapeutic oligopeptide, as defined herein.

The composition of the invention comprises in the range 0.1% to 5% therapeutic oligopeptide. In particular embodiments, the composition comprises 0.5% to 2%, 2.5% or 3% therapeutic oligopeptide. In a preferred embodiment the composition comprises 1% therapeutic oligopeptide. Most preferably the composition comprises 1% CyPep-1, i.e. the composition comprises 1% therapeutic oligopeptide, and the therapeutic oligopeptide is a D-peptide consisting of the amino acid sequence set forth in SEQ ID NO: 1.

The composition of the invention further comprises a preservative. The preservative functions to maintain sterility of the composition (i.e. it has antimicrobial activity). In particular, the preservative may have biocidal properties such that it kills or inhibits the growth of bacteria and fungi, such as yeast. Thus the preservative may have antibacterial and antifungal activity. A particularly preferred preservative is phenoxyethanol.

Phenoxyethanol:

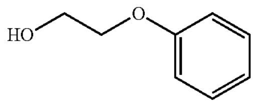

Other suitable preservatives are known in the art and include parabens (including methyl, ethyl, propyl and butyl parabens); sorbic acid (alternatively known as 2,4-hexadienoic acid) and its salts, including sodium sorbate and potassium sorbate; and benzoic acid and its salts, including sodium benzoate and potassium benzoate.

The composition of the invention comprises in the range 0.1% to 5% preservative. In particular embodiments, the composition comprises 0.5% to 2%, 2.5% or 3% preservative. In a preferred embodiment the composition comprises 1% preservative. Preferably the composition of the invention comprises 0.1% to 5% phenoxyethanol. In particular, the composition may comprise 0.5% to 2%, 2.5% or 3% phenoxyethanol. In a particularly preferred embodiment the composition comprises 1% phenoxyethanol.

The composition of the invention further comprises a silicone (polysiloxane). The silicone acts to provide a pleasant texture to the composition. Generally, the silicone used in the composition of the invention is a dimethicone (dimethylpolysiloxane). Dimethicones of different average polymer lengths are distinguished by their differing kinematic viscosities (the longer the average polymer length, the higher the viscosity and vice versa). In the context of dimethicone kinematic viscosity is measured using centistokes (cSt). The SI unit of kinematic viscosity is $m^2/s$. A kinematic viscosity of 1 $m^2/s$ is equivalent to a kinematic viscosity of $10^6$ cSt; conversely, a kinematic viscosity of 1 cSt is equivalent to a kinematic viscosity of $10^{-6}$ $m^2/s$. Viscosity is measured at 25° C. Dimethicones with a wide range of viscosities may be used as an excipient in a pharmaceutical composition. For instance, a viscosity between 20 cSt and 1000 cSt may be suitable, depending on the concentration of the dimethicone in the composition and the desired viscosity of the composition as a whole. It is particularly preferred that the present composition comprises dimethicone with a viscosity of 350 cSt at 25° C. (commonly referred to as dimethicone 350 cSt).

The composition of the invention comprises in the range 0.1% to 5% silicone (preferably dimethicone). In particular embodiments, the composition comprises 0.5% to 2%, 2.5% or 3% silicone (preferably dimethicone). In a preferred embodiment the composition comprises 1% dimethicone. Preferably the composition of the invention comprises 0.1% to 5% dimethicone 350 cSt. In particular, the composition may comprise 0.5% to 2%, 2.5% or 3% dimethicone 350 cSt. In a particularly preferred embodiment the composition comprises 1% dimethicone 350 cSt.

The composition of the invention further comprises di(ethylene glycol) ethyl ether (DEGEE), commonly referred to by its trade name: TRANSCUTOL®-P.

DEGEE:

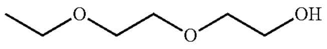

DEGEE has activity as a solvent and a penetration enhancer. By "penetration enhancer" it is meant that DEGEE improves absorption of the active ingredient through the skin, when the composition of the invention is applied to a subject. The composition of the invention comprises in the range 10% to 20% DEGEE. In particular embodiments, the composition comprises 10% to 18%, 10% to 16%, 12% to 20%, 12% to 18%, 12% to 16%, 14% to 20%, 14% to 18% or 14% to 16% DEGEE, preferably 14% to 16% DEGEE. Most preferably the composition comprises 15% DEGEE.

The composition of the invention further comprises butylated hydroxyanisole (BHA). BHA is a mixture of the isomeric compounds 2-tert-butyl-4-hydroxyanisole and 3-tert-butyl-4-hydroxyanisole.

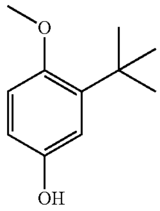

2-tert-butyl-4-hydroxyanisole (left) and

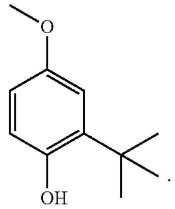

3-tert-butyl-4-hydroxyanisole (right)

The BHA used in the composition of the invention may comprise the 2-tert- and 3-tert- isomers in any ratio. In particular embodiments, the BHA comprises at least 50%, 60%, 70%, 75%, 80%, 85%, 90% or 95% 3-tert-butyl-4-hydroxyanisole.

BHA is an antioxidant, in that it is able to sequester free radicals in the composition in its aromatic ring. This prevents oxidation and degradation of other components of the composition, improving its stability. The composition of the invention comprises in the range 0.005% to 0.1% BHA. In particular embodiments, the composition comprises 0.01% to 0.1%, 0.09%, 0.08%, 0.07%, 0.06% or 0.05% BHA, preferably 0.01% to 0.05% BHA. In further embodiments the composition comprises 0.01% to 0.04% or 0.03% BHA. Most preferably the composition comprises 0.02% BHA.

The composition of the invention further comprises liquid paraffin (also known as mineral oil). Liquid paraffin functions as an emollient (or moisturiser), maintaining hydration of the skin to which the composition is applied. The composition of the invention comprises in the range 1% to 10% liquid paraffin. In particular embodiments, the composition comprises 2% to 10%, 2% to 8%, 2% to 6%, 4% to 10%, 4% to 8% or 4% to 6% liquid paraffin, preferably 4% to 6% liquid paraffin. Most preferably the composition comprises 4.8% liquid paraffin.

The composition of the invention further comprises soft paraffin (also known as petrolatum or petroleum jelly). Either white or yellow soft paraffin (white petrolatum or yellow petrolatum) may be used in the composition of the invention. Preferably white soft paraffin (white petrolatum) is used (white soft paraffin is petrolatum which has been highly refined such that it is essentially decoloured). Soft paraffin (including white soft paraffin) also functions as an emollient.

The composition of the invention comprises in the range 1% to 10% soft paraffin (preferably white soft paraffin). In particular embodiments the composition comprises 1% to 9%, 1% to 7%, 3% to 10%, 3% to 9%, 3% to 7%, 5% to 10%, 5% to 9% or 5% to 7% soft paraffin (preferably white soft paraffin). Preferably the composition comprises 5% to 7% soft paraffin (preferably white soft paraffin). Most preferably the composition comprises 6.3% soft paraffin, in particular 6.3% white soft paraffin.

The composition of the invention further comprises cetostearyl alcohol. Cetostearyl alcohol is a mixture of the solid alcohols cetyl alcohol (hexadecan-1-ol) and stearyl alcohol (octadecan-1-ol). Cetostearyl alcohol functions as emulsifying agent, and thus acts to stabilise the emulsion of the composition of the invention, preventing phase separation.

The proportions of cetyl alcohol and stearyl alcohol in cetostearyl alcohol are variable. Generally, cetostearyl alcohol as used herein may comprise 30-70% of both cetyl alcohol and stearyl alcohol. Cetostearyl alcohol may not be a pure mix of cetyl and stearyl alcohol, but may also include small quantities of other alcohols, e.g. myristyl alcohol. The cetostearyl alcohol may be (approximately) a 70:30, 60:40, 50:50, 40:60 or 30:70 mixture cetyl:stearyl alcohols. Most preferably the cetostearyl alcohol is a 50:50 mixture of cetyl alcohol and stearyl alcohol. Cetostearyl alcohol which is a 50:50 mixture of cetyl alcohol and stearyl alcohol is referred to herein as cetostearyl alcohol 50:50.

The composition of the invention comprises in the range 1% to 10% cetostearyl alcohol (preferably cetostearyl alcohol 50:50). In particular embodiments the composition comprises 2% to 10%, 2% to 8%, 2% to 6.5%, 2% to 6%, 4% to 10%, 4% to 8%, 4% to 6.5%, 4% to 6%, 4.5% to 8%, 4.5% to 6.5%, 4.5% to 6% or 5% to 6% cetostearyl alcohol (preferably cetostearyl alcohol 50:50). In a preferred embodiment the composition comprises 4.5% to 6.5% cetostearyl alcohol (preferably cetostearyl alcohol 50:50). In another preferred embodiment the composition comprises 5% to 6% cetostearyl alcohol (preferably cetostearyl alcohol 50:50). Most preferably the composition comprises 5.5% cetostearyl alcohol, in particular 5.5% cetostearyl alcohol 50:50.

The composition of the invention further comprises polyoxyl 20 cetostearyl ether (also known as ceteareth-20 or macrogol cetostearyl ether). Polyoxyl 20 cetostearyl ether is a mixture of ethoxylated cetyl and stearyl alcohols, each having an average number of ethoxy units between 17.2 and 25. Preferably the ethoxylated cetyl and stearyl alcohols each have an average of 20 ethoxy units. In a particular embodiment, the ethoxylated cetyl and stearyl alcohols both contain 20 ethoxy units. Polyoxyl 20 cetostearyl ether functions as both an emulsifying agent and a nonionic surfactant, promoting the formation and stabilisation of the emulsion of the composition of the invention.

The composition of the invention comprises in the range 0.1% to 5% polyoxyl 20 cetostearyl ether. In particular embodiments, the composition comprises 0.1% to 4%, 0.1% to 3%, 0.5% to 5%, 0.5% to 4%, 0.5% to 3%, 1% to 5%, 1% to 4%, 1% to 3%, 2% to 5%, 2% to 4% or 2% to 3% polyoxyl 20 cetostearyl ether. In a preferred embodiment the composition comprises 1% to 3% polyoxyl 20 cetostearyl ether. In another preferred embodiment, the composition comprises 2% to 3% polyoxyl 20 cetostearyl ether. Most preferably the composition comprises 2.4% polyoxyl 20 cetostearyl ether.

The excipients used in the composition of the invention are generally described in the Handbook of Pharmaceutical Excipients, $6^{th}$ Edition (edited by Raymond C Rowe, Paul J Sheskey and Marian E Quinn, published by the Pharmaceutical Press (UK) and the American Pharmacists Association, 2009). All excipients used are common in the art and are widely available from commercial suppliers. As noted above, the composition of the invention is an aqueous composition, and so where the total amount of the active ingredient and excipients does not total 100% of the composition, the remainder may be made up with water.

The water used in the composition of the invention is sterile. Preferably the water is also deionised. In a preferred embodiment, water for irrigation is used. Water for irrigation is well known in the art. Water for irrigation is hypotonic, with an osmolarity of 0 Osm/L.

In a particular embodiment, the composition of the invention comprises:

(i) 0.1-5% therapeutic oligopeptide, wherein the therapeutic oligopeptide comprises the amino acid sequence set forth in SEQ ID NO: 1, or an amino acid sequence having at least 85% sequence identity thereto;
(ii) 0.1-5% preservative;
(iii) 0.1-5% silicone;
(iv) 10-20% di(ethylene glycol) ethyl ether;
(v) 0.005-0.1% butylated hydroxyanisole;
(vi) 1-10% liquid paraffin;
(vii) 1-10% soft paraffin;
(viii) 1-10% cetostearyl alcohol; and
(ix) 0.1-5% polyoxyl 20 cetostearyl ether.

In another embodiment, the composition of the invention comprises:

(i) 0.1-5% therapeutic oligopeptide, wherein the therapeutic oligopeptide consists of the amino acid sequence set forth in SEQ ID NO: 1 and is an inverso-compound, every amino acid of which is a D-amino acid;
(ii) 0.1-5% phenoxyethanol;
(iii) 0.1-5% dimethicone 350 cSt;
(iv) 10-20% di(ethylene glycol) ethyl ether;
(v) 0.005-0.1% butylated hydroxyanisole;
(vi) 1-10% liquid paraffin;
(vii) 1-10% white soft paraffin;
(viii) 1-10% cetostearyl alcohol 50:50; and
(ix) 0.1-5% polyoxyl 20 cetostearyl ether.

In another embodiment, the composition of the invention comprises:

(i) 0.5-2% therapeutic oligopeptide, wherein the therapeutic oligopeptide comprises the amino acid sequence set forth in SEQ ID NO: 1, or an amino acid sequence having at least 85% sequence identity thereto;
(ii) 0.5-2% preservative;
(iii) 0.5-2% silicone;
(iv) 14-16% di(ethylene glycol) ethyl ether;
(v) 0.01-0.05% butylated hydroxyanisole;
(vi) 4-6% liquid paraffin;
(vii) 5-7% soft paraffin;
(viii) 4.5-6.5% cetostearyl alcohol; and
(ix) 1-3% polyoxyl 20 cetostearyl ether.

In another embodiment, the composition of the invention comprises:

(i) 0.5-2% therapeutic oligopeptide, wherein the therapeutic oligopeptide consists of the amino acid sequence set forth in SEQ ID NO: 1 and is an inverso-compound, every amino acid of which is a D-amino acid;
(ii) 0.5-2% phenoxyethanol;
(iii) 0.5-2% dimethicone 350 cSt;
(iv) 14-16% di(ethylene glycol) ethyl ether;
(v) 0.01-0.05% butylated hydroxyanisole;
(vi) 4-6% liquid paraffin;
(vii) 5-7% white soft paraffin;
(viii) 4.5-6.5% cetostearyl alcohol 50:50; and
(ix) 1-3% polyoxyl 20 cetostearyl ether.

In another embodiment, the composition of the invention consists of:

(i) 1% therapeutic oligopeptide, wherein the therapeutic oligopeptide comprises the amino acid sequence set forth in SEQ ID NO: 1, or an amino acid sequence having at least 85% sequence identity thereto;
(ii) 1% preservative;
(iii) 1% silicone;
(iv) 15% di(ethylene glycol) ethyl ether;
(v) 0.02% butylated hydroxyanisole;
(vi) 4.8% liquid paraffin;
(vii) 6.3% soft paraffin;
(viii) 5.5% cetostearyl alcohol;
(ix) 2.4% polyoxyl 20 cetostearyl ether; and
(x) 62.98% water.

In another embodiment, the composition of the invention consists of:
(i) 1% therapeutic oligopeptide, wherein the therapeutic oligopeptide consists of the amino acid sequence set forth in SEQ ID NO: 1 and is an inverso-compound, every amino acid of which is a D-amino acid;
(ii) 1% phenoxyethanol;
(iii) 1% dimethicone 350 cSt;
(iv) 15% di(ethylene glycol) ethyl ether;
(v) 0.02% butylated hydroxyanisole;
(vi) 4.8% liquid paraffin;
(vii) 6.3% white soft paraffin;
(viii) 5.5% cetostearyl alcohol 50:50;
(ix) 2.4% polyoxyl 20 cetostearyl ether; and
(x) 62.98% water.

The composition of the invention, being a cream, may be provided in a tube (e.g. made of plastic) or a tub or pot (e.g. made of plastic, metal or glass), or any other suitable container.

The present invention further provides a composition as described above for use in therapy. By therapy is meant the treatment of a subject suffering from a disease or medical condition. Generally herein, therapy is used to mean treatment administered in an attempt to cure the subject of the condition from which they are suffering. A subject, as defined herein, refers to any mammal, e.g. a farm animal such as a cow, horse, sheep, pig or goat, a pet animal such as a rabbit, cat or dog, or a primate such as a monkey, chimpanzee, gorilla or human. Most preferably, and in most circumstances, the subject is a human.

The present invention also provides a composition as described above for use in the treatment of a neoplasm. In an embodiment, the invention provides a composition as described above for use in the treatment of a skin neoplasm (i.e. a neoplastic condition of the skin). More particularly, the present invention provides a composition as described above for use in the treatment of a wart. Similarly, the invention provides a method of treating a neoplasm in a subject, comprising administering a composition of the invention to the subject (or more particularly, to the neoplasm). In an embodiment, the invention provides a method of treating a skin neoplasm in a subject, comprising administering a composition of the invention to the subject (or more particularly, to the neoplasm). In particular, the invention provides a method of treating a wart in a subject, comprising administering a composition of the invention to the subject (or more particularly to the wart). Similarly, the invention provides the use of a composition of the invention in the manufacture of a medicament for treating a neoplasm. In an embodiment, the invention provides the use of a composition of the invention in the manufacture of a medicament for treating a skin neoplasm. In particular, the invention provides the use of a composition of the invention in the manufacture of a medicament for treating a wart. That is to say, the composition of the invention is used to treat a subject suffering from a neoplasm of the skin, e.g. a wart (i.e. a subject in need of treatment for a neoplasm, e.g. a wart), in order to destroy or shrink the neoplasm, e.g. wart, and/or to prevent the neoplasm, e.g. wart, from spreading.

The composition of the invention may be used to treat non-malignant neoplastic conditions of the skin, including warts (as described above), actinic keratoses, seborrheic keratoses and Bowen's disease (squamous cell carcinoma in situ). Actinic keratoses (also known as solar keratoses) are non-malignant, rough patches of skin caused by damage to the skin resulting from solar exposure. Seborrheic keratoses are waxy/wart-like growths of unknown cause. Commonly, neither actinic or seborrheic keratoses require treatment. However, treatment may be required if the skin lesions caused by these conditions become irritating. Actinic keratoses can develop into skin cancer, and thus the provision of treatment options for this condition is important in skin cancer prevention. Bowen's disease can turn into malignant squamous cell carcinoma if left untreated. The composition of the invention provides an important new treatment option for these conditions.

The composition of the invention may also be used to treat malignant neoplastic conditions of the skin (i.e. skin cancers). For instance, the composition of the invention may be used to treat squamous cell carcinoma and basal cell carcinoma.

For all the neoplastic skin conditions which the composition of the invention may be used to treat, the composition may be directly (topically) applied to the skin lesions.

As detailed above, the subject treated with the composition of the invention may be any mammal, such as a farm or pet animal, as exemplified above, but is preferably a human. The composition of the invention may be used to treat any human suffering from a neoplasm (e.g. wart), including humans of either gender (male or female), and of any age (adult or child).

As mentioned above, by "wart" as used herein is meant any and all kinds of wart, as described above. In a preferred embodiment, the composition is used in the treatment of cutaneous warts. Cutaneous warts include common warts (verruca vulgaris), verrucas (plantar warts, verruca plantaris), flat warts (verruca plana), intermediate warts (which have features of both common and flat warts), filiform warts and periungual warts. Essentially, all warts apart from anogenital warts are defined herein as cutaneous warts. For instance, the composition of the invention may be used in the treatment of common warts; the composition of the invention may be used in the treatment of plantar warts; the composition of the invention may be used in the treatment of flat warts or intermediate warts; the composition of the invention may be used in the treatment of filiform warts; the composition of the invention may be used in the treatment of periungual warts. In another embodiment, the composition is used in the treatment of anogenital warts.

The composition may be used to treat any number of warts on a subject concurrently. The composition may be used to treat only a single wart, but may alternatively be used to treat several warts at the same time. For instance, two, three, four or five or more warts on a single subjected may be treated at the same time using the composition of the invention. By analogy similar considerations may apply to the treatment of other neoplastic lesions.

The composition of the invention is administered to the subject in need of treatment (e.g. for warts) in a therapeutically effective amount. By "therapeutically effective amount" is meant an amount sufficient to show benefit to the condition of the subject. Whether an amount is sufficient to show benefit to the condition of the subject may be determined by the subject him/herself or a physician/veterinarian. In particular, sufficient of the composition is administered in order to shrink or destroy a treated wart.

Generally, the composition of the invention is administered topically to the subject to be treated. The composition cream is administered directly to the neoplasm, e.g. to the surface of a wart. The cream may be applied to the neoplasm (e.g. wart) by the subject him/herself, by a physician or by a third party, e.g. a relative of the subject such as a parent. The cream may easily be applied directly from the container (e.g. from a tube), or via a finger. Generally, the composition will be applied on each occasion in an amount sufficient to cover the lesion or wart to be treated. Following administration of the cream the lesion or wart may be covered with a plaster or dressing (preferably an occlusive plaster or dressing), in order to retain the cream at the site of the lesion or wart. Where the composition of the invention is used to treat multiple lesions or warts concurrently, the cream is applied separately to each lesion or wart to be treated.

The composition of the invention may be applied to the neoplasm (e.g. warts) to be treated daily, e.g. once daily, twice daily or three times daily. The composition of the invention may alternatively be applied every other day or every third day, or every week. In a preferred embodiment the composition of the invention is applied to the neoplasm/warts to be treated once daily. In another preferred embodiment, the composition is applied to the neoplasm/warts to be treated twice daily. Treatment of neoplasms/warts with the composition of the invention may be for an unspecified duration, e.g. until the neoplasm/wart has been destroyed, that is to say until the treatment has been successful. Alternatively, treatment of warts with the composition of the invention may be for a defined length of time, e.g. for 1, 2, 3, 4, 5, 6, 7, 8, 9, 10, 11 or 12 weeks or more, or about 1, 2, 3, 4, 5, 6, 7, 8, 9, 10, 11 or 12 weeks or more. The treatment may be for 1, 2 or 3 months or more, or about 1, 2 or 3 months or more. For instance, the treatment may be for 2-8 weeks, e.g. 4-8 weeks or 6-8 weeks, 2-4 weeks or 2-6 weeks. In a preferred embodiment, the treatment is for 4 weeks, or thereabouts.

In a particularly preferred embodiment the treatment comprises once daily administration of the cream to a wart to be treated for a period of 4 weeks, or about 4 weeks. In other preferred embodiments, the treatment comprises once daily administration of the cream to a wart to be treated for a period of 2-8 weeks (e.g. 4-8 weeks), or twice daily administration of the cream to a wart to be treated for a period of 2-8 weeks (e.g. 4-8 weeks).

The invention may be further understood by reference to the non-limiting examples below.

FIGURE LEGENDS

FIG. 1 shows the results of calibration experiments to determine CyPep-1 concentration by HPLC (using the method of Example 1). A shows a representative calibration curve of CyPep-1 standards prepared in deionised water over a concentration range of 2.5-500 μg/ml. The points shown in the graph are the mean values of 3 HPLC runs. B shows a sample chromatogram representative of a CyPep-1 calibration standard (in this case with a concentration of 100 μg/ml CyPep-1).

Figure 2:
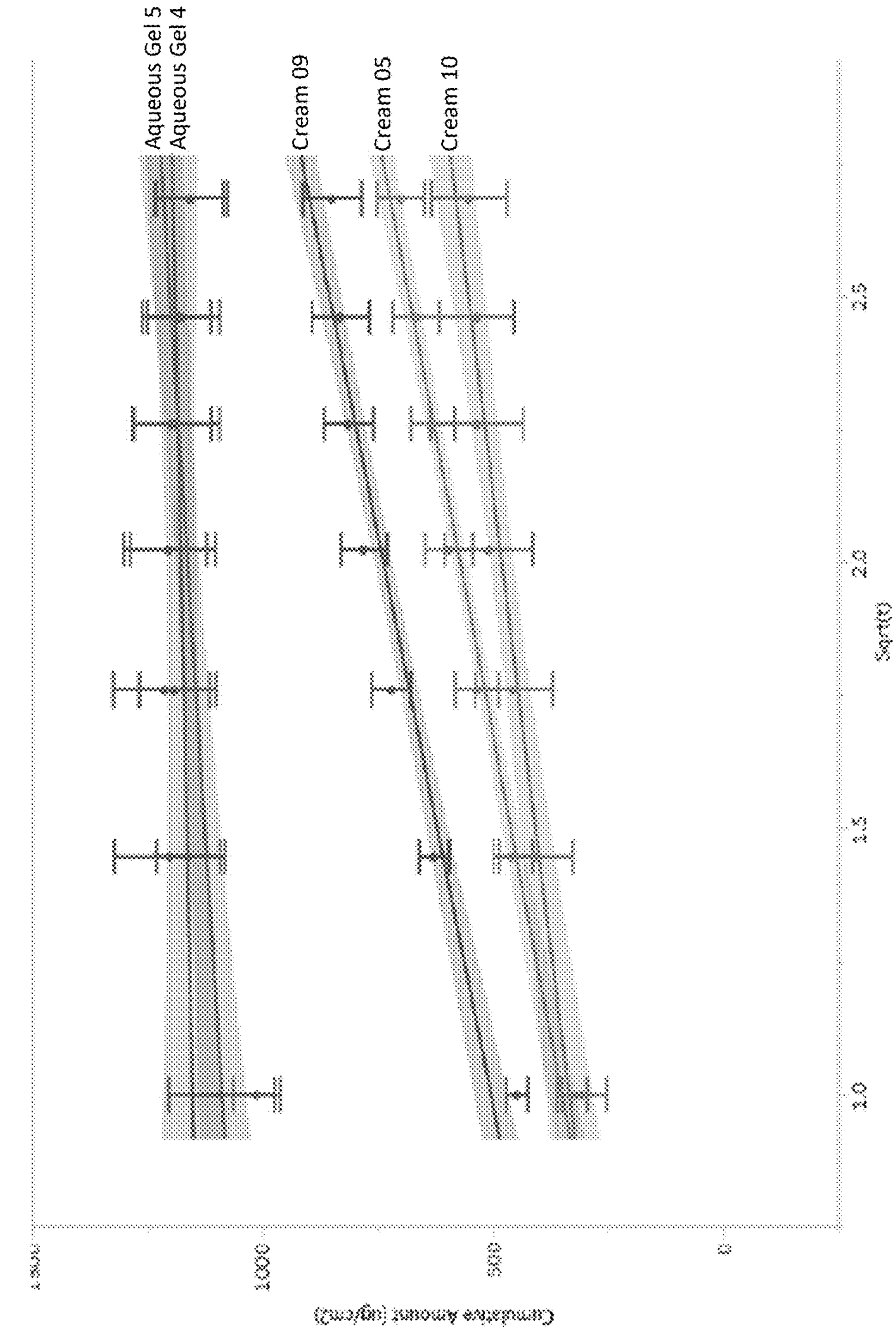

FIG. 2 shows the mean cumulative amount of CyPep-1 released per unit area (μg/$cm^2$) between 1 and 7 hours (presented as the square root of time) from 5 tested pharmaceutical formulations across an isopore membrane into a receptor solution (deionised water). Data presented as mean±standard deviation (n=6).

EXAMPLES

Example 1—Development of Analytical Method

To measure stability of CyPep-1 in the tested pharmaceutical formulations, the following analytical method for quantification of CyPep-1 by HPLC was developed. Various conditions (temperature, flow rate etc.) were tested (data not shown) and the following procedure was found to be optimal.

HPLC was performed using a PHENOMENEX® (USA) KINETEX® C18 5 μm 100 Å 4.6×250 mm column and a PHENOMENEX® SecurityGuard C18 5 μm guard column, as follows:

| | | | |
|---|---|---|---|
| Mobile phase A | 0.05% v/v trifluoroacetic acid in water | | |
| Mobile phase B | 0.05% v/v trifluoroacetic acid in acetonitrile | | |
| Initial flow rate | 1.0 mL/min | | |
| Run time | 30 min | | |
| Wavelength | 276 nm | | |
| Column temperature | 25° C. | | |
| Auto sampler temperature | 5° C. | | |
| | Time (min) | % Mobile Phase A | % Mobile Phase B |
| Flow gradient | 0.00 | 90 | 10 |
| | 3.00 | 90 | 10 |
| | 24.00 | 70 | 30 |
| | 26.00 | 70 | 30 |
| | 26.01 | 90 | 10 |
| | 30.00 | 90 | 10 |
| Injection volume | 25 μL | | |
| Retention time of CyPep-1 | ~19.4 minutes | | |
| Sample and standard diluent | Deionised water | | |
| Seal wash and line storage | 20:80 v/v methanol:water | | |

This HPLC procedure was determined to have a lower limit of quantification of CyPep-1 of 2.5 μg/ml. A representative calibration curve of CyPep-1 standards and a sample chromatogram representative of a calibration standard obtained using the above-described HPLC method are shown in FIGS. 1A and 1B, respectively.

Example 2—Formulation Development

Initial experiments demonstrated high solubility of CyPep-1 in deionised water (pH 4, 5, 6 or 7), ethanol, phenoxyethanol and benzyl alcohol (saturated solubility of CyPep-1 in each of more than 10% w/w). The stability of CyPep-1 in these liquids was tested. Good recovery (at least 95%) of CyPep-1 was observed following 4 weeks storage at 40° C. and 50° C. in deionised water (pH 4-7) and at 40° C. in a mixture of ethanol and phenoxyethanol.

Solubility Testing—Method

The saturated solubility of CyPep-1 in various liquid excipients was assessed as follows:

(i) CyPep-1 (ca. 20.0 mg) was weighed into suitably sized glass vials.

(ii) Each of the excipients (ca. 500 mg) were added to the individual glass vials from Step (i).

(iii) The CyPep-1 and excipient systems were stirred for 24 h (once saturation was observed) in a pre-calibrated water bath at 25° C.

(iv) During the 24 h of stirring the solutions were visually inspected hourly (where possible) to observe if the CyPep-1 had dissolved in the excipients.

(v) If CyPep-1 was observed to dissolve then ca. 20.0 mg increments of CyPep-1 were added to the vial until saturation was reached or until a total of 60 mg had been added at which point the solubility was reported as 10% w/w.

(vi) For saturated systems any un-dissolved CyPep-1 was removed from the saturated solution via centrifugation for 10 min at ca. 16,000×g. A sample of the saturated supernatant was examined using light microscopy with a magnification of 200-1000× using a LEICA® (Germany) DME light microscope. The saturated supernatant was mounted on a microscope slide and examined immediately using both polarised and non-polarised light for the presence of CyPep-1 crystals. The dilution (Step (vii)) was performed immediately after the centrifugation step.

(vii) Since the solubility of CyPep-1 in these excipients was unknown, an appropriate dilution was made to achieve a concentration of CyPep-1 in sample diluent (deionised water) that was above the limit of quantification of the HPLC method, prior to analysis. For excipients which were saturated following the addition of ca. 20 mg of CyPep-1 the following dilution was performed:

(a) Into a 10 mL volumetric flask ca. 50 mg of the saturated solution was weighed.

(b) The volumetric flask from Step (a) was made to volume with sample diluent (deionised water) and vortex mixed for 30 s.

(c) An aliquot of the diluted sample from Step (b) was transferred to an HPLC vial and analysed by HPLC as described above.

(viii) For excipients which were saturated following the addition of ca. 40 mg of CyPep-1 the dilution was performed as detailed in Step (vii), however a 20 mL volumetric flask was used.

Stability Testing—Method

The stability of CyPep-1 was assessed in the liquid excipients which demonstrated a saturated solubility of CyPep-1 above 10% (w/w). The stability of CyPep-1 in the excipients was assessed as follows:

(i) CyPep-1 (40.0±0.1 mg) was weighed into a suitably sized glass vial.

(ii) Each of the excipients (39.96±0.2 g) were added to each of the suitably sized glass vials from Step (i).

(iii) A PTFE magnetic stirrer was added to the mixtures of Step (ii), and left to mix for ca. 16 h.

(iv) The solutions from Step (iii) were transferred to 3 mL borosilicate glass vials with Teflon-lined lids. Sufficient vials were prepared for testing at t=0 and 2 additional time points at 25, 40 and 50° C.; n=1 aliquot per time point was prepared.

(v) Placebo solutions (no added CyPep-1) were also prepared and placed onto stability according to Step (iv).

(vi) The time points assessed were t=0, 2 and 4 weeks, following storage at 40 and 50° C. At each time point the CyPep-1 content and % a/a in the solutions was analysed as follows:

a) Each CyPep-1 solution (500±10 mg) was weighed into three individual 10 mL volumetric flasks.

b) The volumetric flasks were made to volume with sample diluent (deionised water) and thoroughly mixed by vortex mixing for 30 s followed by inversion 5 times.

c) If the excipient was observed to be immiscible with the sample diluent (Step (b)), the extraction was stirred at ambient temperature for ca. 2 h, prior to centrifugation for 10 min at ca. 16,000×g.

d) An aliquot of each sample (from Step (b) or (c)) was transferred to amber HPLC vials and analysed using HPLC as described in Example 1.

e) For the placebo solutions Steps (a) to (d) were followed, however, only one replicate was prepared and analysed.

Based on these initial solubility and stability experiments, several CyPep-1 formulations were synthesised for further testing, as follows:

Cream 01:

| Ingredient | Concentration (% w/w) |
|---|---|
| CyPep-1 | 1 |
| Deionised Water | 24 |
| PEG 400 | 42 |
| Transcutol-P | 12 |
| Benzyl Alcohol | 1 |
| Cetostearyl Alcohol | 5 |
| Crodamol GTCC | 10 |
| Dimethicone | 1 |
| Span-60 | 1.4 |
| Tween-60 | 2.6 |

Cream 02:

| Ingredient | Concentration (% w/w) |
|---|---|
| CyPep-1 | 1 |
| Deionised Water | 24 |
| PEG 400 | 42 |
| TRANSCUTOL ®-P (di(ethylene glycol) ethyl ether) | 12 |
| Benzyl Alcohol | 1 |
| Cetostearyl Alcohol | 5 |
| Crodamol ™ GTCC (caprylic/capric triglyceride) | 10 |
| Dimethicone | 1 |
| BRIJ ®-S2 (steareth-2) | 1.5 |
| BRIJ ®-S20 (steareth-20) | 2.5 |

Cream 03:

| Ingredient | Concentration (% w/w) |
|---|---|
| CyPep-1 | 1 |
| Deionised Water | 24 |
| PEG 400 | 42 |
| TRANSCUTOL ®-P (di(ethylene glycol) ethyl ether) | 12 |
| Benzyl Alcohol | 1 |
| Cetostearyl Alcohol | 5.5 |
| Liquid Paraffin | 4.8 |
| White Soft Paraffin | 6.3 |
| Dimethicone | 1 |
| Ceteareth-20 | 2.4 |

Cream 04:

| Ingredient | Concentration (% w/w) |
|---|---|
| CyPep-1 | 1 |
| Deionised Water | 30 |
| PEG 400 | 32.98 |
| TRANSCUTOL ®-P (di(ethylene glycol) ethyl ether) | 15 |
| Phenoxyethanol | 1 |
| Cetostearyl Alcohol | 5 |
| BHA | 0.02 |
| Crodamol ™ GTCC (caprylic/capric triglyceride) | 10 |
| Dimethicone | 1 |
| BRIJ ®-S2 (steareth-2) | 1.5 |
| BRIJ ®-S20 (steareth-20) | 2.5 |

Cream 05:

| Ingredient | Concentration (% w/w) |
|---|---|
| CyPep-1 | 1 |
| Deionised Water | 78 |
| Phenoxyethanol | 1 |
| Liquid Paraffin | 11.17 |
| Cetostearyl Alcohol | 3.83 |
| Dimethicone | 1 |
| BRIJ ®-S2 (steareth-2) | 1.4 |
| BRIJ ®-S20 (steareth-20) | 2.6 |

Cream 06:

| Ingredient | Concentration (% w/w) |
|---|---|
| CyPep-1 | 1 |
| Deionised Water | 78 |
| Phenoxyethanol | 1 |
| Cetostearyl Alcohol | 5 |
| Crodamol ™ GTCC (caprylic/capric triglyceride) | 10 |
| Dimethicone | 1 |
| BRIJ ®-S2 (steareth-2) | 1.5 |
| BRIJ ®-S20 (steareth-20) | 2.5 |

Cream 07:

| Ingredient | Concentration (% w/w) |
|---|---|
| CyPep-1 | 1 |
| Deionised Water | 77 |
| Benzyl Alcohol | 2 |
| Cetostearyl Alcohol | 5 |
| Crodamol ™ GTCC (caprylic/capric triglyceride) | 10 |
| Dimethicone | 1 |
| BRIJ ®-S2 (steareth-2) | 1.5 |
| BRIJ ®-S20 (steareth-20) | 2.5 |

Cream 08:

| Ingredient | Concentration (% w/w) |
|---|---|
| CyPep-1 | 1 |
| Deionised Water | 78 |
| Phenoxyethanol | 1 |
| Cetostearyl Alcohol | 5.5 |
| Liquid Paraffin | 4.8 |
| White Soft Paraffin | 6.3 |
| Ceteareth-20 | 2.4 |
| Dimethicone | 1 |

Cream 09:

| Ingredient | Concentration (% w/w) |
|---|---|
| CyPep-1 | 1 |
| Deionised Water | 62.98 |
| Phenoxyethanol | 1 |
| TRANSCUTOL ®-P (di(ethylene glycol) ethyl ether) | 15 |
| Cetostearyl Alcohol | 5.5 |
| Liquid Paraffin | 4.8 |
| White Soft Paraffin | 6.3 |
| BHA | 0.02 |
| Ceteareth-20 | 2.4 |
| Dimethicone | 1 |

Cream 10:

| Ingredient | Concentration (% w/w) |
|---|---|
| CyPep-1 | 1 |
| Deionised Water | 41.98 |
| PEG 400 | 35 |
| Benzyl Alcohol | 2 |
| BHA | 0.02 |
| Cetostearyl Alcohol | 5.5 |
| Liquid Paraffin | 4.8 |
| White Soft Paraffin | 6.3 |
| Ceteareth-20 | 2.4 |
| Dimethicone | 1 |

Ointment 1:

| Ingredient | Concentration (% w/w) |
|---|---|
| CyPep-1 | 1 |
| PEG 400 | 58 |
| TRANSCUTOL ®-P (di(ethylene glycol) ethyl ether) | 15 |
| Benzyl Alcohol | 1 |
| PEG 3350 | 25 |

Ointment 2:

| Ingredient | Concentration (% w/w) |
|---|---|
| CyPep-1 | 1 |
| PEG 400 | 49 |
| TRANSCUTOL ®-P (di(ethylene glycol) ethyl ether) | 15 |
| Deionised Water | 10 |
| PEG 4000 | 25 |

Ointment 3:

| Ingredient | Concentration (% w/w) |
|---|---|
| CyPep-1 | 1 |
| PEG 400 | 62.98 |
| Phenoxyethanol | 1 |
| BHA | 0.02 |
| Deionised Water | 10 |
| PEG 4000 | 25 |

Aqueous Gel 1.

| Ingredient | Concentration (% w/w) |
|---|---|
| CyPep-1 | 1 |
| Deionised Water | 30 |
| PEG 400 | 52 |
| TRANSCUTOL ®-P (di(ethylene glycol) ethyl ether) | 15 |
| Benzyl Alcohol | 1 |
| CARBOPOL ® 974 (carboxypolymethylene) | 1 |

Aqueous Gel 2:

| Ingredient | Concentration (% w/w) |
|---|---|
| CyPep-1 | 1 |
| Deionised Water | 96 |
| Benzyl Alcohol | 2 |
| CARBOPOL ® 974 (carboxypolymethylene) | 1 |

Aqueous Gel 3:

| Ingredient | Concentration (% w/w) |
|---|---|
| CyPep-1 | 1 |
| Deionised Water | 96 |
| Benzyl Alcohol | 2 |
| Hydroxyethyl Cellulose | 1 |

Aqueous Gel 4:

| Ingredient | Concentration (% w/w) |
|---|---|
| CyPep-1 | 1 |
| Deionised Water | 85.98 |
| BHA | 0.02 |
| Ethanol | 10 |
| Phenoxyethanol | 1 |
| Hydroxyethyl Cellulose | 2 |

Aqueous Gel 5:

-continued

| Ingredient | Concentration (% w/w) |
|---|---|
| CyPep-1 | 1 |
| Deionised Water | 70.98 |
| BHA | 0.02 |
| Ethanol | 10 |
| TRANSCUTOL ®-P (di(ethylene glycol) ethyl ether) | 15 |
| Phenoxyethanol | 1 |
| Hydroxyethyl Cellulose | 2 |

Non-Aqueous Gel 1:

| Ingredient | Concentration (% w/w) |
|---|---|
| CyPep-1 | 1 |
| PEG 400 | 68.1 |
| Ethanol | 4.9 |
| TRANSCUTOL ®-P (di(ethylene glycol) ethyl ether) | 25 |
| Hydroxypropyl Cellulose | 1 |

Example 3—Formulation Testing

Ointment 1 and Non-Aqueous Gel 1 were immediately discarded, since CyPep-1 proved insoluble in these formulations. Formulations were then centrifuged at 16 minutes. Formulations which separated during that time were deemed unstable and discarded. The following formulations were discarded as deemed unstable due to separation during centrifugation: Cream 01 and Ointment 02. Aqueous Gels 01 and 02 were discarded due to turbidity, indicating the gelling agent (CARBOPOL®974 (carboxypolymethylene)) was not fully hydrated. It was determined that this was due to incompatibility of CARBOPOL®974 (carboxypolymethylene) with CyPep-1. Creams 2 and 3, and Aqueous Gel 3, were also discarded. Stability of CyPep-1 in the various formulations was then investigated.

CyPep-1 Extraction—Method

Prior to stability testing, a CyPep-1 extraction method was generated. Several methods were tested (data not shown). The optimal extraction method developed was performed as follows:

(i) 150 mg formulation was weighed into a 10 ml volumetric flask.

(ii) The flask was made up to volume with 50:50 v/v water:ethanol.

(iii) The volumetric flask was vortex-mixed for 30 s to disperse the formulation, yielding an extraction solution containing CyPep-1 at a concentration of 150 μg/ml.

(iv) A PTFE magnetic stirrer was added to the volumetric flask from Step (iii) and the contents of the volumetric flask was stirred for 2 h at 500 rpm.

(v) The extraction solution from Step (iv) was transferred to centrifuge tubes and the samples were centrifuged at 16,000×g for 10 min at 25° C.

(vi) The supernatant was filtered using a 0.2 μm PTFE filter.

The obtained, filtered solution was used for HPLC analysis. This method was found to recover an estimated 96% of CyPep-1 from the formulations.

Short-Term Stability Testing

The 10 formulations described above which were not discarded were taken into stability testing. Samples of the formulations were stored at 2-8° C., 25° C. and 40° C. After 2 weeks, samples stored at 25° C. and 40° C. were assessed; after 4 weeks and 11 weeks samples stored at 2-8° C. and 25° C. were assessed.

No change in macroscopic (by eye) or microscopic (400× magnification) appearance was seen for any formulation at any time point.

Stability of CyPep-1 in each formulation was determined based on how much CyPep-1 could be recovered at each time point at each temperature. The results are shown in the table below. Data is presented as the mean with the range in brackets (n=2, unless specified elsewhere).

Cream 06: this demonstrated relatively poor stability.

Cream 07: this demonstrated relatively poor stability.

Cream 08: although this showed equal stability to the selected formulations, the formulation does not contain an antioxidant. Oxidation was found to be a potential route of CyPep-1 oxidation (data not shown) and so this formulation was discarded.

Percentage recovery of CyPep-1 (as a percentage of the theoretical concentration) in formulations at t = 0 and following storage for t = 2 weeks at 25 and 40° C. and t = 4 and 11 weeks at 2-8 and 25° C.

| | | T = 2 weeks | | T = 4 weeks | | T = 11 weeks | |
|---|---|---|---|---|---|---|---|
| Formulation | T = 0* | 25° C. | 40° C. | 2-8° C. | 25° C. | 2-8° C. | 25° C. |
| Cream 04 | 103.15 (101.95-105.45) | 95.89 (95.43-96.35) | 66.45 (58.50-74.40) | 98.16 (97.89-98.43) | 96.72 (96.46-96.98) | 101.24 (101.18-101.30) | 106.38 (105.77-107.00) |
| Cream 05 | 100.54 (99.37-101.85) | 96.30 (95.97-96.62) | 77.37 (76.33-78.42) | 93.82 (93.54-94.11) | 97.29 (96.41-98.18) | 93.48 (87.92-99.05) | 98.41 (97.29-99.54) |
| Cream 06 | 101.27 (98.11-105.51) | 94.39 (93.93-94.84 | 70.41 (66.76-74.05) | 97.56 (96.59-98.54) | 88.01 (80.76-95.25) | 97.15 (97.14-97.16) | 95.89 (95.53-96.25) |
| Cream 07 | 101.27 (99.33-103.31) | 91.80 (91.71-91.89) | 73.08 (68.98-77.19) | 95.27 (94.72-95.82) | 94.64 (94.19-95.09) | 95.97 (95.18-96.76) | 92.02 (91.80-92.24) |
| Cream 08 | 100.58 (98.52-103.25) | 97.77 (97.57-97.98) | 73.85 (72.44-75.25) | 96.10 (93.98-98.21) | 97.57 (96.15-99.00) | 99.56 (98.97-100.15) | 96.80 (96.41-97.19) |
| Cream 09 | 100.37 (97.43-104.87) | 99.71 (99.38-100.04) | 76.27 (74.59-77.96) | 96.16 (93.50-98.82 | 98.77 (98.41-99.13) | 100.96 (99.81-102.11) | 97.06 (96.46-97.67) |
| Cream 10 | 100.19 (98.60-102.63) | 98.69 (98.48-98.90 | 78.11 (76.55-79.68) | 101.67 (100.92-102.42) | 101.18 (100.93-101.43) | 102.02 (101.93-102.12) | 101.08 (100.77-101.39) |
| Ointment 3 | 96.21 (96.21-96.21) | 91.94 (91.29-92.58) | 67.83 (66.35-69.30) | 97.27 (96.76-97.77) | 83.57 (81.05-86.09) | 100.69 (99.16-102.23) | 82.50 (82.29-82.71) |
| Aqueous Gel 4 | 94.14 (91.68-96.59) | 102.01 (99.67-104.35) | 100.91 (99.10-102.71) | 100.18 (100.03-100.34) | 98.75 (98.33-99.18) | 97.24 (95.34-99.14) | 105.36 (105.09-105.62) |
| Aqueous Gel 5 | 74.26 (71.04-77.10) | 99.16 (98.09-100.24) | 97.34 (94.75-99.92) | 101.58 (99.97-103.19) | 96.68 (96.03-97.34) | 99.47 (99.42-99.52) | 106.26 (106.18-106.35) |

*n = 3

At t=0 the percentage recovery of CyPep-1 for all of the formulations prepared for short term stability was observed to be 94.14-103.15% of the theoretical concentration. The exception to this was formulation Aqueous Gel 5, which resulted in a recovery of 74.26% of the theoretical concentration of CyPep-1 at t=0. However the results for subsequent time points were between 96.68 and 106.26% of the theoretical concentration of CyPep-1, therefore the result obtained at t=0 was likely to be an anomalous result.

Following storage for t=2 weeks at 40° C. a drop in the recovery of CyPep-1 was observed for all of the cream and ointment formulations assessed (66.45-78.11%). Based on these results, the remainder of the stability assessments were performed at 2-8 and 25° C. as CyPep-1 was deemed to be unstable at 40° C. Following storage for t=2, 4 and 11 weeks at 25° C. and t=4 and 11 weeks at 2-8° C. no substantial changes (<10%) were observed in the percentage recovery of CyPep-1, demonstrating that CyPep-1 was stable in these formulations for up to 11 weeks under the storage conditions tested. The exception to this was Ointment 3 which demonstrated a downwards trend in recovery of CyPep-1 over time when stored at 25° C.

Based on a combination of these results, and the aesthetics of each formulation, the following formulations were selected for further study:

Cream 05
Cream 09
Cream 10
Aqueous Gel 4
Aqueous Gel 5.

The following formulations were discarded:

Cream 04: this demonstrated relatively poor stability, and the formulation was found to be aesthetically poor (off-white and greasy).

Ointment 3: this demonstrated relatively poor stability, and the formulation was found to be aesthetically poor (off-white and greasy).

Example 4—In Vitro Drug Release Testing

CyPep-1 was found to display minimal non-specific binding to glass and plastic, meaning no detergent was required in the receptor solution to prevent non-specific binding. Deionised water was therefore selected as the receptor solution for the study.

Five synthetic membranes were then evaluated for back-diffusion of the formulations. The membranes tested were supor, nitrocellulose, isopore, cellulose and nylon. Only the cellulose membrane demonstrated back diffusion following application of the formulation with deionised water as a receptor solution, potentially altering the composition of the formulation applied. No back diffusion was noted with any other membrane tested.

The same membranes were evaluated for binding of CyPep-1. Recovery of CyPep-1 following incubation with the membranes is shown below (mean recovery, n=3, compared to control with no membrane, incubation at 32° C.):

| Membrane | 24 Hours | 48 Hours | 96 Hours |
|---|---|---|---|
| Supor | 81.53 | 70.39 | 86.13 |
| Nitrocellulose | 74.67 | 65.62 | 76.03 |
| Isopore | 93.61 | 89.52 | 88.61 |
| Cellulose | 38.32 | 18.54 | 18.6 |
| Nylon | 82.77 | 59.6 | 77.54 |

The isopore membrane was selected for use in the drug release study, since CyPep-1 recovery was highest from this membrane, and no back-diffusion was seen with this membrane.

In Vitro Drug Release Experiment—Method

Individually calibrated static Franz cells were employed in the method, each cell having an average surface area and volume of about 2 $cm^2$ and 10 ml, respectively. The static Franz cells were mounted with isopore membrane and filled with deionised water. The static Franz cells were then equilibrated to 32° C. in a water bath, and 30 minutes later dosed with an "infinite dose" (300 $mg/cm^2$) of a test formulation. One Franz cell was mounted with isopore membrane but not dosed with a formulation, in order to act as a blank.

At each time point (0, 1, 2, 3, 4, 5, 6 and 7 hours) a 1 ml aliquot of receiver fluid (deionised water) was removed from the Franz cell using a syringe, via the sampling arm. Each 1 ml aliquot was replaced with 1 ml pre-warmed deionised water, to retain a constant volume, ensuring no bubbles were generated in the cell. Each aliquot removed was analysed by HPLC, using the method described above, and the cumulative amount of CyPep-1 released across the isopore membrane calculated. For the duration of the experiment, the Franz cells were protected from light by occlusion with parafilm.

In Vitro Drug Release Experiment—Results

The amount of CyPep-1 released across the isopore membrane into the receptor solution over the course of the 7 hour experimental period by each formulation is shown in FIG. 2. As shown, The gel formulations Aqueous Gel 4 and Aqueous Gel 5 were observed to release the highest level of CyPep-1 of the tested formulations. These formulations were observed to have a rapid release of CyPep-1 over the initial 1 h experimental period, followed by minimal additional release thereafter. The cream formulations Cream 05, Cream 09 and Cream 10 initially released a lower amount of CyPep-1 at the 1 h time point when compared to the gel formulations, but continued to release CyPep-1 between the 1 and 7 h time points.

These experiments showed that Cream 09 clearly had the most advantageous properties for use as a pharmaceutical. As shown in Example 3, above, CyPep-1 is very stable in this cream. The results shown in Example 4 demonstrate a high level of sustained release of CyPep-1 from the cream. Sustained release of CyPep-1 is desirable, since it means that following a single application of the formulation to a wart CyPep-1 is continuously being released onto the wart, meaning that each application of cream has a long-lasting therapeutic effect. This in turn means that a lower frequency of application of the cream is required than for a formulation such as the tested aqueous gels which release their CyPep-1 content essentially instantaneously, and therefore have only a relatively brief therapeutic effect on the treated wart. Cream 09 releases comfortably the highest level of CyPep-1 of the tested creams (each of which demonstrates sustained release of the peptide), and therefore has the most advantageous properties of all tested formulations, and can be expected to display the highest level of efficacy in wart treatment.

Example 5—Manufacture of Cream 09

Two vessels were utilised during the manufacturing process, Vessel A and Vessel B. Phenoxyethanol and TRANSCUTOL®-P (di(ethylene glycol) ethyl ether) were added to Vessel A, followed by BHA. The contents of the vessel were stirred until BHA was solubilised. Water was then added to Vessel A, followed by CyPep-1. The mixture was stirred until a clear solution was obtained (free from particles or crystals).

The liquid paraffin, soft white paraffin, cetostearyl alcohol and polyoxyl 20 cetostearyl ether were added to Vessel B. The contents of Vessel B were heated to 65° C., and melted. The contents of Vessel A were also heated to 65° C. The contents of Vessel B were then added to Vessel A and homogenised for mins at 10,000 rpm. During the homogenisation process dimethicone was added. The formulation was then cooled to room temperature, while stirring continuously.

Example 6—Wart Treatment with Cream 09

A clinical trial was carried out testing the effect of CyPep-1, in the context of Cream 09, on cutaneous warts. Patients were split into two groups: one group received Cream 09, the other a placebo (Placebo 09, equivalent to Cream 09 except CyPep-1 is replaced with water).

The creams were administered to the patients once daily, by direct topical administration to the treated wart(s), for a duration of 28 days. Following application of the cream, the cream-covered wart was covered with a transparent film for 8-12 hours, to prevent loss of the cream from the wart. Patients were followed up weekly.

The invention claimed is:

1. An aqueous pharmaceutical composition, the composition comprising:

(i) 0.5-2% w/w therapeutic oligopeptide, wherein the therapeutic oligopeptide comprises the amino acid sequence set forth in SEQ ID NO: 1, or an amino acid sequence having at least 85% sequence identity thereto;

(ii) 0.5-2% w/w preservative;

(iii) 0.5-2% w/w silicone;

(iv) 14-16% w/w di(ethylene glycol) ethyl ether;

(v) 0.01-0.05% w/w butylated hydroxyanisole;

(vi) 4-6% w/w liquid paraffin;

(vii) 5-7% w/w soft paraffin;

(viii) 4.5-6.5% w/w cetostearyl alcohol; and (ix) 1-3% w/w polyoxyl 20 cetostearyl ether.

2. The composition of claim 1, wherein the therapeutic oligopeptide comprises or consists of the amino acid sequence set forth in SEQ ID NO: 1.

3. The composition of claim 1, wherein the therapeutic oligopeptide compound is an inverso-compound, every amino acid of which is a D-amino acid.

4. The composition of claim 1, wherein the preservative is phenoxyethanol.

5. The composition of claim 1, wherein the silicone is a dimethicone.

6. The composition of claim 5, wherein the dimethicone is dimethicone with a viscosity of 350 cSt at 25° C. (dimethicone 350 cSt).

7. The composition of claim 1, wherein the cetostearyl alcohol is a 50:50 mixture of cetyl alcohol and stearyl alcohol (cetostearyl alcohol 50:50).

8. The composition of claim 1, wherein the soft paraffin is white soft paraffin.

9. The composition of claim 1, wherein the composition consists of:

(i) 1% therapeutic oligopeptide, wherein the therapeutic oligopeptide consists of the amino acid sequence set forth in SEQ ID NO: 1 and is an inverso-compound, every amino acid of which is a D-amino acid;

(ii) 1% w/w phenoxyethanol;

(iii) 1% w/w dimethicone 350 cSt;

(iv) 15% w/w di(ethylene glycol) ethyl ether;

(v) 0.02% w/w butylated hydroxyanisole;

(vi) 4.8% w/w liquid paraffin;

(vii) 6.3% w/w white soft paraffin;

(viii) 5.5% w/w cetostearyl alcohol 50:50;

(ix) 2.4% w/w polyoxyl 20 cetostearyl ether; and (x) 62.98% w/w water.

10. A method of treating a neoplasm in a subject, comprising administering to the subject the composition as defined in claim 1.

11. The method of claim 10, wherein the neoplasm is a wart.

12. The method of claim 11, wherein the treatment comprises topical administration of the composition to the wart.

13. The method of claim 12, wherein the treatment comprises daily administration of the composition to the wart for a period of about 4 weeks.

14. The method of claim 11, wherein the wart is a cutaneous wart.

15. The method of claim 10, wherein the neoplasm is a neoplasm of the skin.

16. The method of claim 15, wherein the neoplasm of the skin is an actinic keratosis, a seborrheic keratosis, Bowens disease, basal cell carcinoma or squamous cell carcinoma.

* * * * *